United States Patent
Ahlnäs

(10) Patent No.: US 11,685,850 B2
(45) Date of Patent: Jun. 27, 2023

(54) USE OF AQUEOUS SOLUTION OF ORGANIC AMMONIUM CARBOXYLATE IN PREVENTING DUSTING OF FINE MATERIAL AND COMBINATION OF AN AQUEOUS SOLUTION OF ORGANIC AMMONIUM CARBOXYLATE AND FINE MATERIAL

(71) Applicant: Oy Granula Ab Ltd, Kotka (FI)

(72) Inventor: Thomas Ahlnäs, Kotka (FI)

(73) Assignee: Oy Granula Ab Ltd, Kotka (FI)

( * ) Notice: Subject to any disclaimer, the term of this patent is extended or adjusted under 35 U.S.C. 154(b) by 435 days.

(21) Appl. No.: 16/649,688

(22) PCT Filed: Dec. 21, 2018

(86) PCT No.: PCT/FI2018/050977
§ 371 (c)(1),
(2) Date: Mar. 23, 2020

(87) PCT Pub. No.: WO2019/122537
PCT Pub. Date: Jun. 27, 2019

(65) Prior Publication Data
US 2020/0248055 A1 Aug. 6, 2020

(30) Foreign Application Priority Data
Dec. 22, 2017 (FI) ..................................... 20176149

(51) Int. Cl.
*C09K 3/22* (2006.01)
*C04B 20/10* (2006.01)
*C07C 211/63* (2006.01)
*E21F 5/06* (2006.01)
*C04B 103/00* (2006.01)

(52) U.S. Cl.
CPC ............ *C09K 3/22* (2013.01); *C04B 20/1022* (2013.01); *C07C 211/63* (2013.01); *E21F 5/06* (2013.01); *C04B 2103/0075* (2013.01)

(58) Field of Classification Search
CPC ........ C04B 20/1022; C04B 2103/0075; C09K 3/22; E21F 5/06; C01C 1/26; C07C 211/63; C07C 215/40
See application file for complete search history.

(56) References Cited

U.S. PATENT DOCUMENTS

| 2,195,573 | A | 4/1940 | Kritchevsky |
| 4,254,166 | A | 3/1981 | Glanville et al. |
| 4,417,992 | A * | 11/1983 | Bhattacharyya ......... C09K 3/22 252/88.1 |
| 5,290,353 | A | 3/1994 | Goffin et al. |
| 2011/0180746 | A1 * | 7/2011 | Ah .......................... C09K 3/185 252/75 |
| 2012/0111583 | A1 | 5/2012 | Brown et al. |

FOREIGN PATENT DOCUMENTS

| CN | 105778866 A | 7/2016 |
| KR | 101606738 B1 | 3/2016 |
| SU | 1477731 A1 | 5/1989 |
| WO | 2011089322 A1 | 7/2011 |
| WO | 2014131950 A1 | 9/2014 |

OTHER PUBLICATIONS

Finnish Patent and Registration Office, Search Report of Finnish patent application No. FI20176149, dated Jul. 9, 2018, 2 pages.
Kirk-Othmer, Encyclopedia of Chemical Technology, 3rd Ed., vol. 1, p. 944.
Supplementary Partial European Search Report for EP18892446; dated Oct. 25, 2021, 1 p.

* cited by examiner

*Primary Examiner* — Ellen M McAvoy
*Assistant Examiner* — Chantel L Graham
(74) *Attorney, Agent, or Firm* — Meunier Carlin & Curfman LLC

(57) ABSTRACT

The invention relate to use of aqueous solution of organic ammonium carboxylate of formula (I): $[NR^1R^2R^3R^4]^{+n}[R^5(COO)]^{-n}$, in which $R^1$, $R^2$, and $R^3$ are selected from the group composing of hydrogen and methyl, $R^4$ is a $C_1$-$C_4$-alkyl substituted with a hydroxyl group, $R^5$ is hydrogen or methyl and n is 1, as a mist or drops in preventing dusting of fine material and in lowering the freezing point of said aqueous solution on the surface of said fine material or on the surface of dust particles obtained from said fine material by spraying said mist or drops onto fine material or onto dust particles obtained from said fine material to neutralize negatively charged dust particles or by changing negatively charged dust particles into positively charged dust particles, wherein said fine material is selected from the group composing of sand, crushed stone, stone powder, crushed expanded clay, or crushed expanded clay aggregate, crushed cement or concrete, cement or concrete powder, chopped organic material, minerals and metal powder.

20 Claims, No Drawings

USE OF AQUEOUS SOLUTION OF ORGANIC AMMONIUM CARBOXYLATE IN PREVENTING DUSTING OF FINE MATERIAL AND COMBINATION OF AN AQUEOUS SOLUTION OF ORGANIC AMMONIUM CARBOXYLATE AND FINE MATERIAL

PRIORITY

This application is a U.S. national application of the international application number PCT/FI2018/050977 filed on Dec. 21, 2018, and claiming priority of Finnish national application 20176149 filed on Dec. 22, 2017 the contents of both of which are incorporated herein by reference.

FIELD OF INVENTION

The invention relates to a method to prevent dusting of fine material.

The invention relates also to a combination of droplets of organic ammonium carboxylate solution and fine material.

The invention relates to use of an aqueous solution of organic of ammonium carboxylate in controlling dusting of sand, crushed stone, stone powder, crushed expanded clay, or crushed expanded clay aggregate, crushed cement or concrete, cement or concrete powder, chopped organic material, minerals, metal powder and the like. The organic ammonium carboxylate which is used as an aqueous solution is especially adapted for controlling dust formation in applications where the biodegradation and low BOD is also required. Preferably the present invention relates to the use of environmentally benign freezing point depressant compositions for preventing dust formation and for preventing ice formation (anti-icing) within the compositions itself.

BACKGROUND OF INVENTION

Mineral dust and street dust (from street rubble) are serious health problems for example in mining industry and cities. There are also other applications wherein dusting of sand, fine crushed stone and soil will cause mineral dust which is a serious health problem. Dusting causes also damage to equipment and vehicle used for example in mining industry, these include vehicles, electric motors, transport bands etc. Specifically in mining industry mineral, dust will intrude itself into ore silos and transportation vehicles and in mining equipment causing freezing in wintertime.

It has suggested several ways to reduce mineral dust in mining industry. One alternative is to bind mineral dust by means of aqueous or water-borne solutions. However, none of water-borne solutions have been successful so far.

If an aqueous solution is used in dust control, water have a tendency to evaporate after spraying onto surface of crushed stone, sand or soil. This requires usage of relatively large amounts of aqueous solution. Using plenty of water in binding dust will then cause other problems, such as mineral puddling.

One important aspect when using aqueous solutions in controlling mineral dust is possible disturbances brought into mining industry processes alongside with said aqueous solution: especially chlorides of potassium, magnesium, calcium and sodium have a tendency to cause disturbances in ore recovery processes, for example in extraction stages.

One important aspect is also biodegradability of solutions used for controlling mineral dust.

Additionally using aqueous solutions to dust binding may also cause freezing of aqueous solution itself. Freezing point depressant compositions are used widespread for variety of purposes, especially for lowering freezing point of an aqueous system so that ice cannot be formed on surfaces or within the aqueous systems or for melting ice formed in those aqueous systems. However, dust control with freezing point depressant compositions is relatively rare because the effectiveness of the freezing point depressant compositions depends on the molar freezing point lowering effect, the number of ionic species that are made available and to the degree to which the compositions can be dispersed in the liquid phase.

Most freezing point depressant compositions are either based on salts such as sodium chloride or potassium formate or alcohols such as glycols and methanol. Alkali and alkali-earth metal salts of carboxylic acid such as potassium formate, sodium formate, potassium acetate and sodium acetate have found increasing use in the area of deicing mainly due to their low environment impact and low viscosity at minus temperatures. However, using these compositions for controlling dusting in mining industry is not a viable option, because potassium, natrium, magnesium and calcium chlorides may interfere ore recovering process.

GENERAL DESCRIPTION OF THE INVENTION

The above prior art as a starting point, the object of the present invention was to solve or at least to alleviate above mentioned problems.

Thus, the general object of the present invention was to provide an aqueous solution which could be used as a combined freezing point depressant and an aqueous solution for controlling dusting and which is also environmentally benign, and which does not form chlorides which may interfere mining process.

The ideal dusting control agent and freezing point depressant composition adapted to use for mining industry would have following properties:
  it should prevent effectively formation of mineral dust from grounded stones, sand and soil,
  it should be free of mining process disturbing halides such as chlorides of alkali and alkali-earth metals especially chlorides of potassium, sodium, magnesium and calcium,
  it should have relatively low biological (BOD) and chemical oxygen demand (COD),
  it should be effective at low temperatures, i.e. it should have low viscosity and low freezing point,
  it should not cause mineral puddling, that is, it should be effective when used also as relatively small amounts.

The present inventors have surprisingly found that the ideal solution for above mentioned problems relating to reducing mineral dust in air with an aqueous solution and in the same time lowering the freezing point of said aqueous solution itself is to use specific aqueous solution of organic ammonium carboxylate of formula (I), $$[NR^1R^2R^3R^4]^+{}_n[R^5(COO)]^{-n}, \qquad (I),$$

in which $R^1$, $R^2$, and $R^3$ are selected from the group composing of hydrogen and methyl, $R^4$ is a $C_1$-$C_4$-alkyl substituted with a hydroxyl group, $R^5$ is hydrogen or methyl and n is 1,
as a mist or drops in preventing dusting of fine material and in lowering the freezing point of said aqueous solution on the surface of said fine material or on the surface of dust particles obtained from said fine material.

Organic ammonium carboxylate stands for a salt or a complex formed of an ammonium cation and a carboxylic anion. Hence one or more ammonium ions of the salt or complex may be primary ($RNH_3^+$), secondary ($R_2NH_2^+$), tertiary ($R_3NH^+$) or quaternary ($R_4N^+$). The carboxylate ion of the salt or complex may be monovalent ($RCOO^-$) or polyvalent ($R(COO^-)_{n>1}$), and in that case it may also comprise unneutralised carboxyl groups (—COOH). In the latter case, $R^5$ is defined as being substituted with carboxyl.

Since the group $R^5$ is associated with a carboxylate group of formic acid or acetic acid, the ammonium carboxylate of formula (I) is based on formic acid or acetic acid and it can be prepared from such an acid or its salt.

In formula (I), n is 1. Consequently, organic ammonium carboxylates used for controlling mineral dust are based on lower fatty acids.

As mentioned above, the ammonium ion of formula (I) may be primary ($RNH_3^+$), secondary ($R_2NH_2^+$), tertiary ($R_3NH^+$) or quaternary (RN. Typical ammonium ions containing unsubstituted alkyls have been formed from water-soluble amines such as methylamine (g), dimethylamine, trimethylamine, ethylamine, diethylamine, etc.

Ammonium ions containing substituted alkyls have typically been formed from water-soluble amines, whose alkyl(s) may have been substituted with one or more hydroxyl groups. In formula (1), $R_1$ is preferably hydrogen and $R_2$ and $R_3$ have been selected from the group comprising hydrogen and methyl. $R_4$ is $C_1$-$C_4$-alkyl substituted with a hydroxyl group.

Organic ammonium carboxylates formed of lower alkanolamines are hence particularly useful. Among lower alkanolamines we may cite monoethanolamine. Preferable aqueous solutions of ammonium carboxylates of formula (I) contain formic acid, acetic acid and monoethanolamine or trimethylmonoethanolamine. Trimethylmonoethanolamine is also called as acetylcholine.

One important group of useful alkanolamines comprises lower alkyl alkanolamines, such as methyl ethanolamine, dimethylethanolamine. Additional information about useful alkanolamines can be found in the book Kirk-Othmer, Encyclopedia of Chemical Technology 3rd Ed., Vol. 1, p. 944, which is incorporated in this disclosure.

It is particularly recommendable that $R_1$ is hydrogen, $R_2$ and $R_3$ are selected from the group comprising of hydrogen and methyl and $R_4$ is ethyl substituted with a hydroxyl group, preferably 2-hydroxy ethyl. In the most advantageous embodiment, the organic ammonium carboxylate of formula (I) is selected from the group comprising of a salt or a complex of formic acid or acetic acid and monoethanolamine or trimethylethanolamine.

In the practice, ammonium carboxylate of formula (I) is prepared e.g. by mixing an ammonium cation source and a carboxyl anion source in the desired molar ratio, either without a medium or by using an appropriate solvent such as water as a medium. When the starting materials are an amine and an acid, they are simply mixed during gentle heating, if necessary. When the starting materials consist of salts, they are typically dissolved separately in water, and then the solutions are combined. If a salt or a complex thus formed is hydrophobic, it will separate from the water phase as an unctuous or paste-like deposit or a wax-like precipitate, and it can be separated from the water phase by any known methods. When both the starting materials and the formed product are hydrophobic, the preparation can be carried out in an organic solvent instead of water. The freezing point depressant composition used in the invention comprises either fluid composing of ammonium carboxylate of formula (I) without solvent or ammonium carboxylate of formula (I) with appropriate solvent. Preferably solvent is an aqueous solution or a dispersion. Chemical stability: Preliminary results indicate that for instance a fluid pair: ethylene amide-formic acid could under special circumstances react and form amid when no solvent is present. Increasing the temperature favours amid formation. Nearly no esters are formed.

To be exact the invention relates to the method defined in the claims and also a combination of drops of aqueous solution of organic ammonium carboxylate and fine material as defined in the claims.

In the use according to present invention aqueous solution of organic ammonium carboxylate of formula (I):

$$[NR^1R^2R^3R^4]^+{}_n[R^5(COO)]^{-n}, \qquad (I),$$ 

in which $R^1$, $R^2$, and $R^3$ are selected from the group composing of hydrogen and methyl, $R^4$ is a $C_1$-$C_4$-alkyl substituted with a hydroxyl group, $R^5$ is hydrogen or methyl and n is 1, as a mist or drops in preventing dusting of fine material and in lowering the freezing point of said aqueous solution on the surface of said fine material or on the surface of dust particles obtained from said fine material, by spraying said mist or drops onto fine material or onto dust particles obtained from said fine material to neutralize negatively charged dust particles or by changing negatively charged dust particles into positively charged dust particles, wherein said fine material is selected from the group composing of sand, crushed stone, stone powder, crushed expanded clay, or crushed expanded clay aggregate, crushed cement or concrete, cement or concrete powder, chopped organic material, minerals and metal powder.

The claimed method, usually comprises also controlling the hydrophobicity and the hydrophilicity of the fine material and dust particles obtained from said fine material which control is based on the concentration of ammonium carboxylate in aqueous solution of formula (I).

Preferably the concentration of ammonium carboxylate in the aqueous solution of formula (I) to be sprayed onto fine material or onto dust particles obtained from said fine material is in the range of 1-50% wt, depending on the water content of the fine material or dust particles obtained from said fine material.

More preferably the concentration of organic ammonium carboxylate in the aqueous solution of formula I is in the range of 1-7% wt-%, still more preferably in the range of 2-5 wt-%.

Preferably the concentration of organic ammonium carboxylate of formula I which is then present on the surface of fine material or dust particles obtained from said fine material present is in the range of 1-7% wt-%, preferably in the range of 2-5 wt-%. The freezing point of the aqueous solution of organic ammonium carboxylate of formula (I) is then in the range of −5 to −50° C.

The invention also relates to the use of aqueous solution of organic ammonium carboxylate of formula (I)

$$[NR^1R^2R^3R^4]^+{}_n[R^5(COO)]^{-n}, \qquad (I),$$ 

in which $R^1$, $R^2$, and $R^3$ are selected from the group composing of hydrogen and methyl, $R^4$ is a $C_1$-$C_4$-alkyl substituted with a hydroxyl group, $R^5$ is hydrogen or methyl and n is 1, as a solution in immersing fine material into said solution, wherein said fine material is selected from the group consisting of sand, crushed stone, expanded clay, expanded clay aggregate (LECA), crushed cement or concrete, chopped organic material and minerals in lowering the freezing point of said aqueous solution.

In the combination according to present invention there exists droplets of aqueous solution of organic ammonium carboxylate of formula (I).

In a combination of mist or drops of aqueous solution of organic ammonium carboxylate of formula (I)

$$[NR^1R^2R^3R^4]^+{}_n[R^5(COO)]^{-n}, \qquad (I),$$ 

in which $R^1$, $R^2$, and $R^3$ are selected from the group composing of hydrogen and methyl, $R^4$ is a $C_1$-$C_4$-alkyl substituted with a hydroxyl group, $R^5$ is hydrogen or methyl and n is 1, and said fine material selected from the group composing of sand, crushed stone, stone powder, crushed expanded clay, or crushed expanded clay aggregate, crushed cement or concrete, cement or concrete powder, chopped organic material, minerals and metal powder, said aqueous solution of organic ammonium carboxylate of formula (I) has been sprayed as a mist or drops onto the surface of said fine material particles, or onto dust particles obtained from said fine material particles to neutralize negatively charged dust particles or by changing negatively charged dust particles into positively charged dust particles.

Preferably the ammonium carboxylate solution to be sprayed as a mist is an aqueous solution contains 1-10% w/w, preferably 2-5% w/w of ammonium carboxylate, for example 3-4% ammonium carboxylate in water. However, this amount may be modified on the basis of moisture content of the fine material or dust particles. The exact concentration of ammonium carboxylate, present on the surface of fine material or dust cannot be measured exactly because water is evaporating continuously from the surface of fine material or dust.

In a case fine material already exists as a coarse dust, which tends to form an aerosol with the surrounding air, it has usually a negative charge. Typical coarse dust is mineral dust (for example zinc or nickel dust), cement or concrete dust, sand dust, stone dust, organic material dust (for example peat dust or wood dust). By using aqueous ammonium carboxylate solution as a fine mist, the negative charge of coarse dust particles can be neutralized and/or converted due to effect of positively charged ammonium ion to dust particles. By using mist of aqueous ammonium carboxylate solution neutralized dust particles from air will then be settled down onto ground.

The average particle size of coarse dust which is treated with the mist of aqueous ammonium carboxylate solution is so called coarse dust P10. Coarse dust P10 has an average particle size typically between 0.125-0.25 mm (125-25 um) and most particles have diameter over 10 um (over 0.010 mm). The mist of aqueous ammonium carboxylate solution should have particle size under 1.5 times of average particle size of coarse dust. More preferably, the average particle size of aqueous ammonium carboxylate solution mist is about the same as the average particle size of coarse dust.

Mist is understood herein to mean droplets or drops having an average diameter under 40 um (under 0.04 mm).

The neutralized coarse dust has then lowered freezing point because an aqueous ammonium carboxylate mist will act as a freezing point depressant on a surface neutralized dust particles.

In a case most fine material (sand, crushed stone, crushed concrete, crushed cement minerals, chopped organic material, metal powder etc.) have mostly a bigger particle size than coarse dust, the aqueous solution of organic ammonium carboxylate can also be applied using other application methods than spraying as a mist. Possible application methods for aqueous solution of organic ammonium carboxylate are: spraying aqueous ammonium carboxylate solution as drops onto fine material, immersion of fine material into ammonium carboxylate solution.

The aqueous ammonium carboxylate solution drops are understood here to have average diameter of 40-500 um (0.4-5 mm).

The aqueous solution of organic ammonium carboxylate (3-5% solution) has a freezing point from −3° C. to −15° C., preferably from 5 to −10° C. However, after applied the solution as a mist or drops onto surface of fine material (for example crushed stone) the water will evaporate from said aqueous solution. This will automatically lower the freezing point of remaining water in said combination of water and organic ammonium carboxylate: as can be seen later from (table IV) freezing point of aqueous solution of organic ammonium carboxylate of formula (I) will be considerably lowered when water leaves and rest of fluid comes more concentrated.

In one preferable use, aqueous solution of organic ammonium carboxylate of formula (I) is used as a mist or drops 1.0-2.0-l per 1000 kg of crushed stone, preferably 1.2-1.5 l per 1000 kg of crushed stone.

One important use of the present invention relates to immersion of fine material into aqueous solution of organic ammonium carboxylate of formula (I):

$$[NR^1R^2R^3R^4]^+{}_n[R^5(COO)]^{-n}, \quad (I),$$

in which $R^1$, $R^2$, and $R^3$ are selected from the group composing of hydrogen and methyl, $R^4$ is a $C_1$-$C_4$-alkyl substituted with a hydroxyl group, $R^5$ is hydrogen or methyl and n is 1. Fine material is selected from the group consisting of sand, crushed stone, expanded clay, expanded clay aggregate (LECA), crushed cement or concrete, chopped organic material and minerals in lowering the freezing point of said aqueous solution.

Advantageously said fine material is crushed expanded clay, crushed expanded clay aggregate, crushed peat, zinc powder, nickel powder, crushed cement or crushed concrete.

In the combination according to present invention there exists droplets of aqueous solution of organic ammonium carboxylate of formula (I):

The aqueous solution of organic ammonium carboxylate is compatible with an ammonium salts of $C_1$-$C_6$ monocarboxylic acids or carboxylates of urea or ethylene glycol or propylene glycol, or glycerol or a mixture thereof. We include in the invention the use of combinations of the ammonium carboxylate of formula (I) with an ammonium salts of $C_1$-$C_6$ monocarboxylic acids or urea or ethylene glycol or propylene glycol, or glycerol or a mixture thereof carboxylates. By using aqueous solution of organic ammonium carboxylate with freezing point depressant composition with urea for de-icing or anti icing applications one can lower oxygen demand on the environment.

The aqueous solution of organic ammonium carboxylate of formula (I) may contain auxiliary substances as well. Typical auxiliary substances comprise such as additional corrosion inhibitors, biocides, coloring agents, surfactants, and viscosity intensifiers. The concentration of auxiliary substances will be in the range of 0.001 to 10 wt-% from the total weight of aqueous solution.

In a preferred embodiment of the invention the aqueous solution of organic ammonium carboxylate of formula (I) has a concentration of sodium, potassium, calcium and magnesium of 0 M. This means that there will be no chlorides formation from these cations after said aqueous solution has been applied for controlling dusting in mines.

Once applied onto surface of above defined fine material, drying of said combination will lead on the one hand to water loss and on the other hand absorbing of water by way of the organic ammonium carboxylate of formula (I) resulting in keeping the surface of said fine material moist. Actually, organic ammonium carboxylate of formula (I) will absorb water after water content of said aqueous solution has dropped at or below 15 wt-%. This is a very important aspect of the present invention, because it will reduce drastically the amount of aqueous solution of organic ammonium carboxylate of formula (I) needed to keep dusting in control after applied onto fine material surface.

Biodegradability of aqueous solutions of the invention used for controlling dusting is relatively low: droplets of aqueous solution of organic ammonium carboxylate of formula (I), and fine material, wherein carboxylate originate from acetic acid, in form of fluid have BOD (biological oxygen demand) of 0.64 mg of 02 at 20° C. for liter of said fluid in 5 days. COD (chemical oxygen demand) for the same combination 0.64 mg 02 at 20° C. for liter of said fluid in 5 days.

DESCRIPTION OF PREFERRED EMBODIMENTS OF THE INVENTION

The invention is described below in greater details with the help of examples. Person skilled in the art will recognize that the properties of the compositions studied are such that they will make ideal mineral dust control aqueous solutions having also freezing point depressant properties for binding dusting of streets, ore mines, horse tracks etc.

In the following non-restricting examples, we have presented some specific applications and properties of aqueous solutions comprising organic ammonium carboxylate of formula (I) as well as combinations comprising aqueous solution of organic ammonium carboxylate of formula (I) and fine material selected from the group composing of sand, crushed stone, minerals and metal powder.

Example 1

An ionogenic solution for controlling mineral dust formation was prepared by mixing 1 mole of formic acid (99%) with 1 mole of monoethanolamine (99%). Distilled water was added to the fluid mixture in order to made 3-5% by weight aqueous solution.

The freezing point of the solution was below −5° C., the electrical conductivity of the fluid was 61 mS/cm at 26° C., and pH of the fluid was 7.55 (measured directly from the solution).

Example 2

An aqueous solution was prepared by mixing 1 mole of formic acid (99%) with 1 mole of monoethanolamine (99%). Distilled water was added to the fluid mixture in order to made 3-5 by weight solution in water.

The freezing point of the solution was below −5° C., the Brookfield DV-I viscosity (20 rpm) was 10 mPas at −20° C., 10 mPas at −10° C., 10 mPas at 0° C., and Bohlin VOR viscosity (shear rate 23.1 1/s) was 4 mPas at 10° C., 3 mPas at 20° C., 2 mPas at 40° C., and 1.5 mPas at 60° C. The electrical conductivity of the fluid was 65 mS/cm at 26° C., and pH of the fluid was 7.54 (measured directly from the solution).

Example 3A

Aqueous ammonium carboxylate solution mixture presented in examples 6 and 7 (below) was used in controlling dusting of crushed stone. This mixture comprises of ethanolamine in acetic acid and ethanolamine in formic acid (1:1). This mixture was sprayed as a 3-5% (w/w) aqueous solution in a form of mist or as drops onto surface of crushed stone and crushed stone dust. The sprayed mixture binds some moisture and prevented mineral dust and stone dust forming aerosol with surrounding air thus effectively preventing dusting by preventing forming charged dust particles. Additionally, it lowered freezing of mineral dust and crushed stone/stone dust.

Crushed stone can be, for example, ore mineral originated from mining industry or rubble which have been gathered from town streets. Instead of above-mentioned mixture comprising ethanolamine in acetic acid and ethanolamine in formic acid, one can also use aqueous ammonium carboxylate solution from example 2 (monoethanolamine and formic acid) or cholineamine in acetic acid or cholineamine in formic acid.

Committed peat material/peat dust and wood dust can also be treated in a similar way as crushed stone. Depending on the particle size of wood dust or committed peat/peat dust the aqueous ammonium carboxylate will be sprayed as a mist or as drops onto surface of peat/peat dust or wood dust. Ammonium carboxylate was sprayed as a 3-5% (w/w) aqueous solution. The concentration present in the surface of committed peat material/peat dust and wood dust cannot be measured exactly because water is evaporating from the surface of fine material or dust.

Example 4

Aqueous ammonium carboxylate solution mixture presented in examples 6 and 7 (below) was used in controlling dusting of crushed stone (street rubble) in situ. For this reason, said aqueous ammonium carboxylate solution mixture was sprayed as drops onto pavement or city street. The concentration of ammonium carboxylate can be from 3% w/w up to 85% w/w calculated from the weight of the total aqueous ammonium carboxylate solution.

The sprayed mixture bound moisture and prevented crushed stone dust from forming gas-solid-particle-aerosol with surrounding air by neutralizing charged crushed stone dust particles. Additionally, this mixture lowered freezing point of crushed stone dust particles. This melts ice and snow which otherwise would have formed on crushed stone.

Example 5A

Aqueous ammonium carboxylate solution mixture presented in examples 6 and 7 or example 2 was used in controlling dusting of crushed stone gathered from town street (street rubble): crushed stone was immersed into aqueous ammonium carboxylate solution (ammonium carboxylate concentration was 3-5% w/w). After this treatment the crushed stone can be reused.

Example 5B

Aqueous ammonium carboxylate solution mixture presented in examples 6 and 7 or example 2 was used as a concentrated solution 50% w/w or 85% w/w by immersing crushed stone into said aqueous ammonium carboxylate solution (immersion solution). The actual concentration of immersion solution changed continuously during the immersion treatment because the fine material absorbs different amount ammonium carboxylate and water. Actual concentration of immersion solution varied from 5% w/w to 85% w/w.

After this treatment the crushed stone was applied onto frozen street. The ammonium carboxylate solution on the surface of crushed stone melted the ice and was diluted by means of melted water. After freezing crushed stone formed an excellent grit onto frozen street.

Instead of crushed stone also expanded clay, or expanded clay aggregate can also be treated in a similar way. Expanded clay or expanded clay aggregate can be applied onto pavements in a similar way as crushed stone in city streets.

Examples 6 and 7

Solutions in examples 6 and 7 have been made in the same way as presented in examples 1-2, that is, by mixing 1 mole of an ammonium cation source and 1 mole of a carboxyl anion source (unless otherwise shown) together for obtaining a concentrated fluid and then adding water to the concentrated fluid, for obtaining diluted solutions.

TABLE 1

In table 1 has been shown formation of possible precipitates from fluids and diluted solutions obtained from fluids. Temperature was 20-25° C.

| Code/ex | fluid | fluid Wt-% from solution 100 | 90 | 80 | 60 | 40 | 20 | 5 | pH of 2% solution |
|---|---|---|---|---|---|---|---|---|---|
| EAE/6 | ethanolamine/ acetic acid | Clear | Clear | Clear | Clear | Clear | Clear | Clear | 6.8 |
| EAM/7 | ethanolamine/ formic acid | Clear | Clear | Clear | Clear | Clear | Clear | Clear | 3.7 |

TABLE 2

The fluid and solution samples from selected examples of table 1 were subjected to chilling to a temperature of +4° C. and then to further cooling to a temperature of −20° C. In these temperatures the possible turbidity, precisipation of these samples was observed.

| ex | | 100 | 90 | 80 | 60 | 40 | 20 | 5 |
|---|---|---|---|---|---|---|---|---|
| | Temperature +4 C. | | | | | | | |
| 6 | ethanolamine/ acetic acid | Clear | Clear | Clear | Clear | Clear | Clear | Clear |
| 7 | ethanolamine/ formic acid | Clear | Clear | Clear | Clear | Clear | Clear | Clear |
| | Temperature of −20° C. | | | | | | | |
| 6 | ethanolamine/ acetic acid | Clear/ liquid state | Clear/ liquid state | Clear/ liquid state | Clear/ liquid state | Clear/ liquid state | frozen | frozen |
| 7 | ethanolamine/ formic acid | Clear/ liquid state | Clear/ liquid state | Clear/ liquid state | Clear/ liquid state | frozen | frozen | frozen |

As can be seen from table 1 and table 2 water-based solutions of organic of ammonium carboxylates are clear solutions independent whether they are diluted or not. This means that when they are used in controlling mineral dust, they have no tendency to salt out after sprayed onto surface of crushed stones, sand, soil or metal. Therefore, they do not interfere with, for example vehicle brakes or transport belts used in mining processes.

TABLE 3

In table 3 has been given results from viscosity measurements compositions of examples 6 and 7. Viscocity was measured with Bohlin method (bold numbers) at shear rate 23.1 1/s and with Brookefield method (normal numbers) at shear rate 20 rpm. Additionally electrical conductivity, ph and redox potential was measured for these compositions comprising fluids and solutions prepared from these fluids by adding distilled water.

| Composition: monoethanolamine/ acetic acid water | fluid Wt-% from solution water wt-% | 100 0 | 90 10 | 80 20 | 60 40 | 40 60 | 20 80 | 5 95 |
|---|---|---|---|---|---|---|---|---|
| | ° C. | VISCO-SITY mPas | | | Bohlin VOR viscosity Brookfield DV-I viscosity | | shear rate 23.1 1/s 20 rpm sp3 | |
| viscosity mPas/ | −20 | | | | | | | |
| | (repeat) | >20000 | >20000 | 12450 | 170 | 35 | X | X |
| | −20 | >20000 | 16740 | 1700 | 80 | 20 | X | X |
| | −10 | >20000 | 5150 | 700 | 60 | 15 | 10 | 5 |
| | 0 | 27850 | 2160 | 330 | 40 | 10 | 10 | 5 |
| | 10 | 15250 | 1152 | 210 | 23 | 6 | 2 | 1.7 |
| | 20 | 5665 | 556 | 118 | 15 | 5 | 2 | 1.3 |
| | 40 | 1220 | 154 | 41 | 8 | 3 | 1.5 | 1.1 |
| | 60 | 345 | 63 | 20 | 5 | 2 | 1 | 0.7 |

TABLE 3-continued

In table 3 has been given results from viscosity measurements compositions of examples 6 and 7. Viscocity was measured with Bohlin method (bold numbers) at shear rate 23.1 1/s and with Brookefield method (normal numbers) at shear rate 20 rpm. Additionally electrical conductivity, ph and redox potential was measured for these compositions comprising fluids and solutions prepared from these fluids by adding distilled water.

| | | | | | | | | |
|---|---|---|---|---|---|---|---|---|
| conductivity mS/cm | | 0.534 | 2.24 | 7.1 | 25.9 | 46.9 | 47.8 | 20.2 |
| T° C. | | 25.4 | 25.9 | 26 | 25.6 | 25.4 | 25.1 | 24.9 |
| pH° C. 22 | | 7.96 | 7.81 | 7.68 | 7.34 | 7.07 | 6.87 | 6.79 |
| REDOX | | +31 | +54 | +69 | +107 | +146 | +179 | +216 |
| Composition: monoethanolamine/ formic acid water | fluid Wt-% from solution water wt-% | 100 0 | 90 10 | 80 20 | 60 40 | 40 60 | 20 80 | 5 95 |
| | pale oily light liquid ° C. | VISCO-SITY mPas | | | Bohlin VOR viscosity Brookfield DV-I viscosity | | shear rate 23.1 1/s 20 rpm sp3 | |
| viscosity mPas/ | −30 | | | | | | | |
| | −20 | 4350 | 680 | 230 | 30 | 10 | X | X |
| | −10 | 2830 | 410 | 130 | 20 | 10 | 5 | X |
| | 0 | 1335 | 240 | 75 | 15 | 10 | 5 | 5 |
| | 10 | 646 | 123 | 41 | 9 | 4 | 2 | 1.5 |
| | 20 | 325 | 72 | 26 | 6 | 3 | 1.7 | 1.2 |
| | 40 | 119 | 31 | 13 | 4 | 2 | 1.2 | 0.95 |
| | 60 | 47 | 17 | 7 | 3 | 1.5 | 1.1 | 0.9 |
| conductivity mS/cm | | 15.9 | 27.3 | 40.4 | 61 | 65 | 46.9 | 16 |
| T° C. | | 26.1 | 25.9 | 25.8 | 25.6 | 25.5 | 25.5 | 25.8 |
| pH/22° C. | | 7.75 | 7.67 | 7.6 | 7.55 | 7.54 | 7.53 | 7.51 |
| REDOX potential | | −321 | −244 | −164 | −110 | −75 | −48 | +4 |

As can be seen from table 3 the viscosity of compositions varies considerably depending on the quality of the fluid in a composition and fluid-solvent proportion (w/w). No solid crystals will be formed for instance if one uses combination ethanol amine/formic acid. Avoiding solid crystals is also a beneficial property for instance for an aqueous solution used for dust control.

Table 4A.
The freezing points of aqueous solutions of organic ammonium carboxylate of formula (I), wherein $R^5$ = H (formiate):
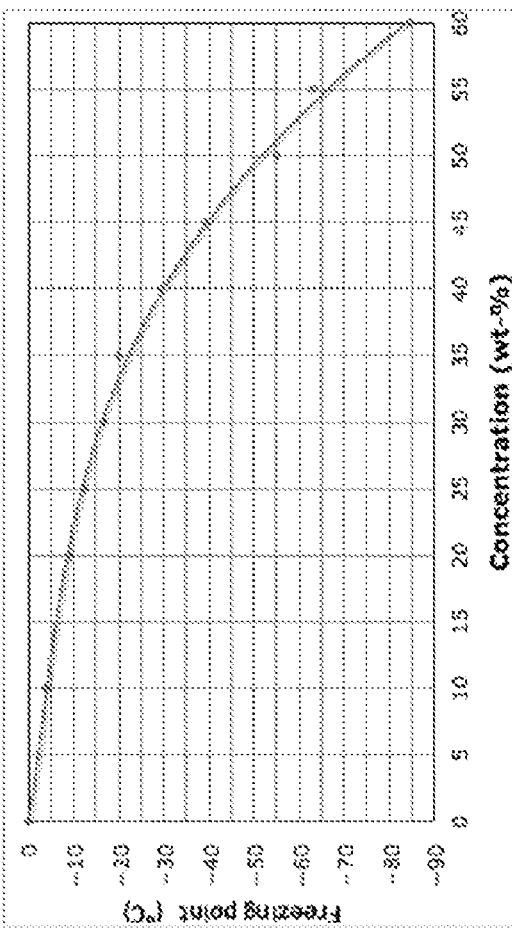

TABLE 4B

The freezing points of selected aqueous solutions of organic ammonium carboxylate of formula (I), wherein $R^5$ = H (formiate) is given in table 4B. Samples of organic ammonium carboxylate of formula (I) in water and their freezing points:

| Sample | Concentration (wt-%) | Freezing point (° C.) |
|---|---|---|
| Water | 0 | 0 |
| HTF-20 | 20 | −8.96 |
| HTF-25 | 25 | −12.44 |
| HTF-30 | 30 | −16.51 |
| HTF-35 | 35 | −20.13 |
| HTF-40 | 40 | −29.33 |
| HTF-45 | 45 | −39.48 |
| HTF-50 | 50 | −54.95 |
| HTF-55 | 55 | −63.01 |
| HTF-60 | 60 | −84.50 |

As can be seen from tables 4A and 4B as the concentration of water solutions of organic ammonium carboxylate of formula (I) increases it will readily lead to lower freezing points. For example, those aqueous solutions of organic ammonium carboxylate of formula (I) presented in tables 4A and 4B having concentration about 10 wt-% have a freezing point about −5° C. However, when the concentration of organic ammonium carboxylate of formula (I) in the aqueous solution increases, the freezing point of the aqueous solutions falls considerably, for example when the concentration of aqueous solution is 30 (wt-%) the freezing point of said aqueous solution is about −20° C. When the concentration of aqueous solution is 60 (wt-%) the freezing point of said aqueous solution is about −85° C. The freezing point of −5° C. corresponds to the freezing point of aqueous solutions of organic ammonium carboxylate of formula (I) which are ready-to-use (1-7 wt % aqueous solution). The freezing point of −30° C. and −85% corresponds the freezing point of the aqueous solution of organic ammonium carboxylate of formula (I) which—has been sprayed onto surface of fine material when water has been evaporated.

The invention claimed is:

1. A method to prevent dusting of fine material selected from the group consisting of sand, crushed stone, stone powder, crushed expanded clay, crushed expanded clay aggregate, crushed peat, wood powder, chopped wood, crushed cement, crushed concrete, cement powder, cement dust, concrete powder, concrete dust, chopped organic material, minerals, metal powder, metal dust, and any combination thereof, the method comprising:
providing an aqueous solution of organic ammonium carboxylate of formula (I):

in which $R^1$, $R^2$, and $R^3$ are independently selected from the group consisting of hydrogen and methyl, $R^4$ is a $C_1$-$C_4$-alkyl substituted with a hydroxyl group, $R^5$ is hydrogen or methyl, and n is 1,
defining an average particle size of the fine material; and
selecting average droplet size for application of the solution based on the defined average particle size such that
when the average particle size is 125-25 μm, neutralizing negatively charged dust particles or changing negatively charged dust particles into positively charged dust particles is caused by applying said aqueous solution as a mist having an average mist droplet size less than 1.5 times of the average particle size onto the fine material or onto dust particles obtained from the fine material; and when the average particle size is more than 400 μm neutralizing negatively charged dust particles or changing negatively charged dust particles into positively charged dust particles is caused by spraying the aqueous solution as droplets having an average droplet size of 0.4-5.0 mm onto the fine material.

2. The method of claim 1, which additionally comprises controlling the hydrophobicity and the hydrophilicity of the fine material and dust particles obtained from said fine material which control is based on the concentration of ammonium carboxylate in aqueous solution of formula (I).

3. The method of claim 1, wherein the concentration of ammonium carboxylate in the aqueous solution of formula (I) to be sprayed onto fine material or onto dust particles obtained from said fine material is in the range of 1-50% wt, depending on the water content of the fine material or dust particles obtained from said fine material.

4. The method of claim 3, wherein the concentration of organic ammonium carboxylate in the aqueous solution of formula I is in a range of 1-10 wt-%, preferably in the range of 2-5 wt-%.

5. The method of claim 4, wherein the concentration of aqueous organic ammonium carboxylate of formula (I), is selected so, that after the aqueous solution of organic ammonium carboxylate of formula (I) has absorbed water from a surface of the fine material or dust particles obtained from said fine material a water content of the aqueous solution of organic ammonium carboxylate of formula (I) is 85 wt-% or less.

6. The method of claim 5, wherein the concentration of organic ammonium carboxylate of formula I present on the surface of fine material or dust particles obtained from said fine material is in a range of 1-10% wt-%, preferably in the range of 2-5 wt-%.

7. The method of claim 1, wherein a surface of the fine material or surface of dust particles obtained from said fine material is hydrophilic after application of the aqueous solution of organic ammonium carboxylate of formula (I).

8. The method of claim 1, wherein the aqueous solution of organic ammonium carboxylate of formula (I) simultaneously acts as a freezing point depressant.

9. The method of claim 1, wherein the aqueous solution of organic ammonium carboxylate of formula (I) contains distilled water only.

10. The method of claim 1, wherein the concentration of sodium, potassium, calcium and magnesium is 0 M in the aqueous solution of organic ammonium carboxylate of formula (I).

11. The method of claim 1, wherein the aqueous solution of organic ammonium carboxylate of formula (I) is additionally admixed with compounds selected from the group comprising glycols, preferably ethylene glycol or propylene glycol, glycerols and viscosity modifying polymers, so that said aqueous organic ammonium carboxylate composition contains 5 to 97.5 wt-% of water.

12. The method of claim 1, wherein the aqueous solution of organic ammonium carboxylate of formula (I) is additionally admixed with auxiliary substances such as additional corrosion inhibitors, biocides, fragrance(s), coloring agents, surfactants, and viscosity intensifiers, so that the concentration of auxiliary substances is in a range of 0.001 to 10 wt-% from the total weight of aqueous solution.

13. The method of claim 1, wherein the aqueous solution of organic ammonium carboxylate of formula (I) contains formic acid, acetic acid and monoethanolamine or trimethylmonoethanolamine.

14. The method of claim 1, wherein 1.0 to 1.5 liters of the aqueous solution of organic ammonium carboxylate of formula (I) is used per 1000 kg of crushed stone.

15. The method of claim 1, further including a step wherein the aqueous solution of organic ammonium carboxylate of formula (I) is prepared by diluting, in situ, concentrated solution of water and organic ammonium carboxylate of formula (I) with water, in which concentrated solution the concentration of organic ammonium carboxylate of formula (I) is 50 wt-% or 85 wt-%.

16. The method of claim 1, further including a step wherein the aqueous solution of organic ammonium carboxylate of formula (I) is prepared by mixing, in situ, an aqueous solution of 1-5 wt-% of amine with an aqueous solution of 1-5 wt-% of acid.

17. A neutral combination of mist or drops of aqueous solution of organic ammonium carboxylate of formula (I):

$$[NR^1R^2R^3R^4]^+_n[R^5(COO)]^{-n}, \quad (I),$$

in which $R^1$, $R^2$, and $R^3$ are selected independently from the group consisting of hydrogen and methyl, $R^4$ is a $C_1$-$C_4$-alkyl substituted with a hydroxyl group, $R^5$ is hydrogen or methyl and n is 1, and fine material selected from the group consisting of sand, crushed stone, stone powder, crushed expanded clay, crushed expanded clay aggregate, crushed peat, wood powder, chopped wood, crushed cement, crushed concrete, cement powder, cement dust concrete powder, concrete dust, chopped organic material, minerals, metal powder, metal dust, and any combination thereof, wherein negatively charged dust particles have been neutralized or changed into positively charged dust particles by spraying the aqueous solution of organic ammonium carboxylate of formula (I) as a mist having average droplet size of less than 1.5 times average particle size of the fine material when the average particle size of the fine material is 125-25 μm, or as drops having average size of 0.4-5 mm when average particle size of the fine material is over 0.4 mm onto the surface of said fine material particles, or onto dust particles obtained from said fine material particles.

18. The neutral combination of claim 17, comprising drops of aqueous solution of organic ammonium carboxylate of formula (I) and fine material, wherein organic ammonium carboxylate of formula (I) will absorb water after water content of said aqueous solution have dropped at or below 15 wt-%.

19. The neutral combination of claim 17 wherein carboxylate originates from acetic acid, in form of fluid and having BOD (biological oxygen demand) of 0.64 mg of $O_2$ at 20° C. for liter of said fluid in 5 days.

20. The neutral combination of claim 17, wherein carboxylate originates from acetic acid, in form of fluid, and having COD (chemical oxygen demand) of 0.64 mg $O_2$ at 20° C. for liter of said fluid in 5 days.

* * * * *